US008906966B2

(12) United States Patent
Sherwood et al.

(10) Patent No.: US 8,906,966 B2
(45) Date of Patent: Dec. 9, 2014

(54) MEDICAMENTS CONTAINING PANTHENOL

(76) Inventors: Paul Sherwood, London (GB); David Keith Davies, Kent (GB)

(*) Notice: Subject to any disclaimer, the term of this patent is extended or adjusted under 35 U.S.C. 154(b) by 0 days.

(21) Appl. No.: 11/777,583

(22) Filed: Jul. 13, 2007

(65) Prior Publication Data

US 2008/0125492 A1 May 29, 2008

Related U.S. Application Data

(60) Provisional application No. 60/847,038, filed on Sep. 25, 2006.

(30) Foreign Application Priority Data

Jul. 13, 2006 (GB) .................................. 0613841.7

(51) Int. Cl.
*A61K 31/164* (2006.01)
*A61P 19/02* (2006.01)

(52) U.S. Cl.
CPC ............ *A61K 31/164* (2013.01); *Y10S 514/825* (2013.01)
USPC .......... 514/625; 514/825; 514/16.8; 514/16.6

(58) Field of Classification Search
CPC .... A61K 31/164; A61K 31/197; A61P 23/02; A61P 19/02
USPC ................. 514/625, 825, 16.8, 16.6
See application file for complete search history.

(56) References Cited

U.S. PATENT DOCUMENTS

| 2,780,645 | A | | 2/1957 | Wehrmeister | |
| 2,845,456 | A | | 7/1958 | Kagan | |
| 2,934,428 | A | | 4/1960 | Donaldson et al. | |
| 4,568,547 | A | | 2/1986 | Herschler | |
| 4,619,829 | A | | 10/1986 | Motschan | |
| 4,743,596 | A | | 5/1988 | Lapin | |
| 4,870,061 | A | | 9/1989 | Speck | |
| 5,260,289 | A | * | 11/1993 | Hyodo et al. ................. | 514/161 |
| 5,360,821 | A | * | 11/1994 | Leung ........................... | 514/563 |
| 6,133,249 | A | | 10/2000 | Hills | |
| 2005/0136085 | A1 | * | 6/2005 | Bellamy ....................... | 424/401 |
| 2007/0191484 | A1 | * | 8/2007 | Sherwood et al. ............ | 514/561 |

FOREIGN PATENT DOCUMENTS

| EP | 0214947 | 3/1987 |
| GB | 1145623 | 3/1969 |
| GB | 2286528 | 8/1995 |
| WO | WO0072823 | 12/2000 |
| WO | WO01/19359 | 3/2001 |
| WO | WO0141783 | 6/2001 |

OTHER PUBLICATIONS

Kozlova et al (AA-Union scientific -research vitamin institute, Moscow, translated from Khimko famratsevtischeskii Shurnal, vol. 11, No. 44, pp. 69-71, Apr. 1977.*
Matt, Joint injections for Arthritis, eOrthopod, Aug. 14, 2003.*
Gado et al, Annals of Rheumatic diseases, vol. 52, pp. 215-218, 1993.*
Babst et al. , Anesthesia Progress, May-Jun. 1978, pp. 87-91.*
Panthenol definition 2003 (Downloaded from the internet on Nov. 9, 2011, Dated 2003, URL: http://web.archive.org/web/20031103082400/http://sci-toys.com/ingredients/panthenol.html.*
CH682803 with English translation.*
Barton-Wright, "Pantothenic acid metabolism in Rheumatoid Arthritis" Chemical Abstracts 60:77820 (1963).
Beers, M. H. et al., "The Merck Manual" Apr. 1999, pp. 445-447.
Bollow, M. et al, "CT-Guided Intraarticular Corticosteroid Injection into the Sacroiliac Joints in Patients with Spondyloarthropathy: Indication and Follow-Up with Contrast-Enhanced MRI", *Journal of Computer Assisted Tomography*, vol. 20, No. 4, pp. 512-521 (1996).
Eagleson, M., "Concise Encyclopedia Chemistry", Walter de Gruyter Berlin, New York, pp. 775-776, (1994).
Fernandez-Palazzi, M.D. Federico et al., "Intraarticular Dexamethasone in Advanced Chronic Synovitis in Hemophilia", *Clinical Orthopaedics and Related Research*, No. 343, pp. 25-29 (1997).
Hills, B.A., "Remarkable Anti-Wear Properties of Joint Surfactant", *Annals of Biomedical Engineering*, vol. 23, No. 2, pp. 112-115 (1995).
Horikiri, Kazuya et al, "Local irritation test on the intraarticular administration of dibucaine hydrochloride injection (Neo Vitacain) in rabbits", Oyo Yakuri (1992) 44(3), 303-7 (Abstract only; 1992: 626235 HCAPLUS; 117: 226235).
Moiseenok, A. G. et al., "Anti Inflammatory and Coenzymic Activity of Pantothenic Acid Derivatives in Adjuvant Arthritis", Khimiko-Farmatsevticheskii Zhurnal, vol. 15, No. 6, pp. 76-81 (1981) (Abstract only; 1982: 305378 BIOSIS; BA74: 77858).
Yurgilevich, V. P. et al., "Some prerequisites to the use of pantothenic acid preparations in the complex therapy of rheumatism", Khim. Biokhim. Funkts. Primen. Pantotenovoi Kisloty, Mater. Grodn. Simp., 4$^{th}$ (1977) (Abstract only; 1979: 432794 HCAPLUS; 91: 32794).
Ostman-Smith et al., "Dilated cardiomyopathy due to type II X-linked 3-methylglutaconic aciduria: successful treatment with pantothenic acid," Br Heart J 1994, 72:349-353.
Kevin J. Saliba et al., "Provitamin B$_5$ (Panthenol) Inhibits Growth of the Intraerythrocytic Malaria Parasite," Antimicrobial Agents and Chemotherapy, 49(2):632-637 (2005).
Adele M. Lehane et al., "Feedback Inhibition of Pantothenate Kinase Regulates Pantothenol Uptake by the Malaria Parasite," The Journal of Biological Chemistry 282(35):25395-25405 (2007).

* cited by examiner

*Primary Examiner* — Savitha Rao
(74) *Attorney, Agent, or Firm* — Fish & Richardson P.C.

(57) ABSTRACT

This invention relates to medicaments and their use in the alleviation of inflammation and pain in joints.

11 Claims, No Drawings

MEDICAMENTS CONTAINING PANTHENOL

CROSS REFERENCE TO RELATED APPLICATIONS

This application claims the benefit of U.S. Provisional Application No. 60/847,038, filed on Sep. 25, 2006 and Great Britain Patent Application No.: GB 0613841.6, filed on Jul. 13, 2006, both of which are incorporated by reference in their entireties.

TECHNICAL FIELD

This invention relates to medicaments and their use in the alleviation of inflammation and pain in joints.

BACKGROUND

Pain or loss of movement in joints is a common occurrence, particularly among the elderly or those who have suffered damage to cartilage, bone surfaces or ligaments. Conventional methods of treatment include the administration of corticosteroids by injection into the site of the inflammation. However, relief tends to be temporary and long term use can carry a number of contraindications.

SUMMARY

It has now been found that panthenol (or a prodrug thereof), when injected into an affected joint or in the region of an affected joint (e.g., a joint affected by, e.g., inflamed by, traumatic arthritis), can be used to treat (e.g., control, ameliorate, alleviate, reduce, eliminate, prevent, slow the progression of, or delay the onset of) pain or inflammation associated with the affected joint.

In one aspect, this invention relates to the use of panthenol (e.g., dexpanthenol) in the preparation of a pharmaceutical composition for administration by injection into or adjacent to a joint for alleviation of inflammation or pain due to traumatic arthritis.

In one aspect, this invention relates to a method of treating pain in a joint inflamed by traumatic arthritis which includes injecting a solution that includes an effective amount (e.g., at least about 100 milligrams (mg), at least about 250 mg, at least about 500 mg, or at least about 1000 mg) of panthenol (or a prodrug thereof) into the inflamed joint, or injecting the solution into a site that is next to the inflamed joint but outside the capsule of the inflamed joint.

Embodiments can include one or more of the following features.

The joint can be affected by a disorder selected from tennis elbow, housemaid's knee, frozen shoulder, inflamed knee joints, and hip and/or back pain associated with inflammation or restricted movement in the spinal vertebrae (e.g., inflammation of spinal vertebrae).

The panthenol can be administered as an aqueous solution. The injectable pharmaceutical composition (e.g., solution, e.g., aqueous solution) can include an aqueous solution of panthenol.

The solution can be injected into a site that is next to the inflamed joint but outside the capsule of the inflamed joint. For example, the solution is injected into a site that is outside the capsule of the inflamed joint and within about 10 millimeters from the exterior surface of the capsule of the joint.

The panthenol can be the dextrorotatory isomer of panthenol (dexpanthenol). In other embodiments, a panthenol racemic mixture or an optically active panthenol enantiomer mixture that includes >50% of the dextro enantiomer can be administered.

The panthenol can be co-administered with a local anesthetic. In some embodiments, the local anesthetic can be co-administered as a separate injection. In other embodiments, the panthenol can be co-formulated with a local anesthetic. The local anesthetic can be bupivacaine.

The injectable pharmaceutical composition (e.g., solution, e.g., aqueous solution) can be a formulation that includes about 1000 milligrams (mg) of panthenol (e.g., dexpanthenol). The injectable pharmaceutical composition (e.g., solution, e.g., aqueous solution) can further include a local anesthetic (e.g., bupivacaine, e.g., about 5 mg of bupivacaine). The injectable pharmaceutical composition (e.g., solution, e.g., aqueous solution) can be a formulation that includes about 1000 milligrams (mg) of dexpanthenol and about 5 mg of bupivacaine.

The panthenol can be co-administered with cysteine or glucosamine.

The injectable composition (e.g., aqueous solution) of the panthenol can be injected into the joint. The solution (e.g., aqueous solution) can be injected directly into the site of the joint. The solution (e.g., aqueous solution) can be injected directly into the inflamed joint.

The inflamed joint can be a freely moving joint that is inflamed by traumatic arthritis.

In some embodiments, the subject can be a subject in need thereof (e.g., a subject identified as being in need of such treatment). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject is a human.

The term "mammal" includes organisms, which include mice, rats, cows, sheep, pigs, rabbits, goats, and horses, monkeys, dogs, cats, and preferably humans.

"An effective amount" refers to an amount of a compound that confers a therapeutic effect (e.g., treats, controls, ameliorates, prevents, delays the onset of, or reduces the risk of developing a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.001 mg/Kg to about 1000 mg/Kg, (e.g., from about 0.01 mg/Kg to about 1000 mg/Kg from about 0.1 mg/Kg to about 1000 mg/Kg).

The details of one or more embodiments of the invention are set forth in the accompanying drawings and the description below. Other features and advantages of the invention will be apparent from the description and from the claims.

DETAILED DESCRIPTION

Panthenol

As used herein, the term "panthenol" refers to a compound having the following chemical structure:

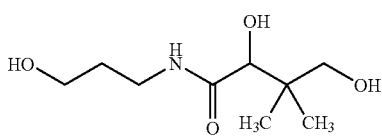

Panthenol is a chiral molecule that contains one stereogenic center. As such, there are two possible optically active, enantiomeric forms of panthenol, i.e., the dextrorotatory isomer (dextro) and the levorotatory isomer (levo). The preferred enantiomeric form of panthenol is the dextro enantiomer (sometimes referred to herein as dexpanthenol). The term "panthenol" includes both enantiomeric forms as well as mixtures thereof (e.g., the stereoisomeric mixtures described herein); and all tautomeric and rotamer forms.

In some embodiments, panthenol can be obtained from pantothenic acid, which is a naturally occurring substance in plant and animal tissue. A particularly rich source of pantothenic acid is royal jelly obtainable from honey bee colonies. Synthetic methods of preparation of pantothenic acid include those described in U.S. Pat. Nos. 2,780,645; 2,845,456 and 2,934,428. As can be appreciated by the skilled artisan, further methods of synthesizing panthenol will be evident to those of ordinary skill in the art. See, e.g., R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof. Panthenol can also be obtained commercially.

In some embodiments, the methods can include administering optically active dextro-panthenol that is substantially free of levo-panthenol.

In some embodiments, the methods can include administering a racemic (i.e., an optically inactive) mixture of panthenol (i.e. 50% of the dextro-enantiomer and 50% of the levo-enantiomer).

In some embodiments, the methods can include administering an optically active mixture of panthenol that is other than a racemic mixture and which contains >50% of the dextro isomer. For example, the methods can include administering an enantiomer mixture having at least about 60% (e.g., at least about 70%, at least about 75%, at least about 80%, at least about 85%, at least about 90%, at least about 95%, at least about 99%) of dextro-panthenol.

In some embodiments, the panthenol may be used in the form of a prodrug. Examples of prodrugs include esters (e.g., derivatives in which one, two, or three of the panthenol hydroxyl groups is capped with an acyl group, such as an acetyl group or a substituted or unsubstituted benzoyl group) and other pharmaceutically acceptable derivatives, which, upon administration to a subject, are capable of providing active compounds.

Pharmaceutical Compositions

In general, panthenol can be administered in the form of a composition, which can further include any conventional non-toxic pharmaceutically-acceptable diluents, carriers, adjuvants or vehicles. In certain embodiments, compositions can further include one or more additional therapeutic agents. In general, the compositions are in a form that is suitable for injection.

The term "pharmaceutically acceptable diluent, carrier, adjuvant, or vehicles" refers to a diluent, carrier, adjuvant or vehicle that may be administered to a subject (e.g., a patient), together with panthenol, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, water, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

Methods of Treatment

Conditions

The methods described herein can be used for the treatment of several conditions associated with inflammation or reduced movement of joints (e.g., arthritic conditions, e.g., treatment of pain associated with these conditions).

In some embodiments, the methods can be used to treat pain in one or more joints of a subject that are affected by (e.g., inflamed by) traumatic arthritis or post-traumatic arthritis. As used herein, the term "traumatic arthritis" refers to arthritis that is caused from blunt, penetrating, or repeated trauma or from forced inappropriate motion of a joint or ligament. Symptoms of traumatic arthritis can include swelling, pain, tenderness, joint instability, and internal bleeding. In certain embodiments, the methods described herein can be used to treat a traumatic arthritic or a post-traumatic arthritic condition that typically occurs in only one joint at a time.

In certain embodiments, the methods described herein can be used to treat, or treat joints affected by (e.g., alleviate pain in a joint affected by), e.g., tennis elbow, housemaid's knee, frozen shoulder, inflamed knee joints and hip pain and back pain (e.g., associated with inflammation or restricted movement in the spinal vertebrae, e.g., post-traumatic spondylitis).

In certain embodiments, the joint(s) can be affected by traumatic arthritis or post-traumatic arthritis, but not osteoarthritis (e.g., primary or secondary osteoarthritis) or rheumatoid arthritis. By way of example, the methods described herein can be used after the onset of traumatic arthritis in the affected joint, but prior to the onset of osteoarthritis (e.g., primary or secondary osteoarthritis) in the affected joint.

In certain embodiments, the methods can be used to treat a traumatic or post-traumatic condition resulting from an injury where the bone and cartilage of the knee do not heal properly.

In certain embodiments, the methods can be used to treat a traumatic or post-traumatic condition that develops after a serious fracture, torn ligament or a tear to the meniscus. For example, the methods can be used to treat a traumatic or post-traumatic condition that develops after a serious hip injury or fracture (e.g., an injury or fracture that can lead to avascular necrosis, in which the blood supply to the ball portion (the femoral head) of the thighbone is cut off and the bone begins to wither).

In certain embodiments, the methods can be used to provide temporary relief from pain associate with rheumatoid arthritis.

Affected Joints

As used herein, the term "joint" (or articulation) refers to the location at which two bones make contact or articulate. The methods described herein can be used to treat a variety of joints that are found in the human or animal body, such as "partly" or "slightly movable" joints or articulations (sometimes referred to as "amphiarthroses") or "freely movable" joints or articulations (sometimes referred to as "diarthroses" or "sinovial"). For purposes of clarification, the above-mentioned descriptors are intended to describe the different, art-recognized physiological categories of joints that can be treated (if affected) using the methods of the invention. The above-mentioned descriptors as used in this context are not intended to describe the condition or performance level or ability of the affected joint.

In some embodiments, the affected joint can be a "partly" or "slightly movable" joint or articulation that is affected by one or more of the conditions described herein (e.g., traumatic arthritis). As used herein, the terms "partly" or "slightly movable joint or articulation" and "amphiarthroses" refer to joints or articulations in which the contiguous bony surfaces are either connected by broad flattened disks of fibrocartilage, of a more or less complex structure, e.g., in the articulations between the bodies of the vertebrae; or are united by an interosseous ligament, e.g., as in the inferior tibiofibular articulation.

In some embodiments, the affected joint can be a "freely movable joint or articulation" that is affected by one or more of the conditions described herein (e.g., traumatic arthritis). As used herein, the terms "freely movable joint or articulation" or "diarthroses" refer to joints or articulations in which the contiguous bony surfaces are covered with articular cartilage, and connected by ligaments lined by synovial membrane. The joint may be divided, completely or incompletely, by an articular disk or meniscus, the periphery of which is continuous with the fibrous capsule while its free surfaces are covered by synovial membrane. Such joints are typically capable of uniaxial, biaxial or polyaxial movement. In certain embodiments, the affected joint can include as part of its normal, physiological structure a space (synovial cavity) between the articulating bones (a sinovial joint).

In certain embodiments, the affected joint can be a ball and socket joint (sometimes referred to as "enarthrosis" or "spheroidal joint") that is affected by one or more of the conditions described herein (e.g., traumatic arthritis). As used herein, the term "ball and socket joint" refers to a joint formed by the reception of a globular head into a cup-like cavity, in which the distal bone is capable of motion around an indefinite number of axes, which have one common center. Nonlimiting examples of ball and socket joints include hip and shoulder joints.

In certain embodiments, the affected joint can be a condyloid joint (sometimes referred to as "condyloid articulation" or "ellipsoidal joint") that is affected by one or more of the conditions described herein (e.g., traumatic arthritis). As used herein, the term "condyloid joint" refers to a joint in which an ovoid articular surface, or condyle, is received into an elliptical cavity in such a manner as to permit of flexion, extension, adduction, abduction, and circumduction, but generally no axial rotation. A nonlimiting example of a condyloid joint is a wrist-joint.

In certain embodiments, the affected joint can be a saddle joint (sometimes referred to as "sellar joint" or "articulation by reciprocal reception") that is affected by one or more of the conditions described herein (e.g., traumatic arthritis). As used herein, the term "saddle joint" refers to a joint in which the opposing surfaces are reciprocally concavo-convex. The movements associated with a saddle joint are similar to those permitted for a condyloid joint. A nonlimiting example of a saddle joint is the carpometacarpal joint of the thumb.

In certain embodiments, the affected joint can be a hinge joint (sometimes referred to as "ginglymus") that is affected by one or more of the conditions described herein (e.g., traumatic arthritis). As used herein, the term "hinge joint" refers to a joint in which the articular surfaces are moulded to each other in such a manner as to permit motion generally in one plane, forward and backward, the extent of motion at the same time being considerable. The direction which the distal bone takes in this motion is typically not in the same plane as that of the axis of the proximal bone; there is usually a certain amount of deviation from the straight line during flexion. The articular surfaces of such joints can be connected together by relatively strong collateral ligaments, which form their chief bond of union. Nonlimiting examples of hinge joints include the interphalangeal joints and the joint between the humerus and ulna (elbow); the knee and ankle joints can also be included, even though they allow a slight degree of rotation or side-to-side movement in certain positions of the limb.

In certain embodiments, the affected joint can be a pivot joint (sometimes referred to as "trochoid joint" or "rotary joint") that is affected by one or more of the conditions described herein (e.g., traumatic arthritis). As used herein, the term "pivot joint" refers to a joint in which (where the movement is limited to rotation) the joint is formed by a pivot-like process turning within a ring, or a ring on a pivot, the ring being formed partly of bone, partly of ligament. For example, in the proximal radioulnar articulation, the ring is formed by the radial notch of the ulna and the annular ligament; here, the head of the radius rotates within the ring. As another example, in the articulation of the odontoid process of the axis with the atlas the ring is formed in front by the anterior arch, and behind by the transverse ligament of the atlas; here, the ring rotates around the odontoid process.

In certain embodiments, the affected joint can be a gliding joint (sometimes referred to as "arthrodial joint" or "plane articulation") that is affected by one or more of the conditions described herein (e.g., traumatic arthritis). As used herein, the term "gliding joint" refers to a joint which admits of only gliding movement; it is typically formed by the apposition of plane surfaces, or one slightly concave, the other slightly convex, the amount of motion between them being limited by the ligaments or osseous processes surrounding the articulation. Nonlimiting examples of gliding joints include the joints between the articular processes of the vertebrae, the carpal joints, except that of the capitate with the navicular and lunate, and the tarsal joints with the exception of that between the talus and the navicular.

Modes of Administration

Dosages

In some embodiments, the methods can include administration of from about 100 milligrams to about 2000 milligrams (e.g., about 100, about 200, about 250, about 300, about 400, about 500, about 600, about 700, about 800, about 900, about 1000, about 11100, about 1200, about 1300, about 1400, about 1500, about 1600, about 1700, about 1800, about 1900, or about 2000 milligrams) of panthenol (or a prodrug thereof).

In some embodiments, the methods can include administration of from about 400 milligrams to about 2000 milligrams (e.g., about 400, about 500, about 600, about 700, about 800, about 900, about 1000, about 1100, about 1200, about 1300, about 1400, about 1500, about 1600, about 1700, about 1800, about 1900, or about 2000 milligrams) of panthenol (or a prodrug thereof).

For ease of exposition, it is understood that any recitation of ranges or subranges of a particular range expressly includes each of the individual values that fall within the recited range, including the upper and lower limits of the recited range.

In some embodiments, the methods can include administration of from about 100 milligrams to about 2,000 milligrams (e.g., from about 100 milligrams to about 2,000 milligrams, from about 100 milligrams to about 1800 milligrams, from about 100 milligrams to about 1600 milligrams, from about 100 milligrams to about 1400 milligrams, from about 100 milligrams to about 1200 milligrams, from about 100 milligrams to about 1100 milligrams, from about 100 milligrams to about 1000 milligrams, from about 100 milligrams to about 900 milligrams, from about 100 milligrams to about 800 milligrams, from about 100 milligrams to about 700 milligrams, from about 100 milligrams to about 600 milligrams, from about 100 milligrams to about 500 milligrams, from about 100 milligrams to about 400 milligrams, from about 100 milligrams to about 300 milligrams) of panthenol.

In some embodiments, the methods can include administration of from about 200 milligrams to about 2,000 milligrams (e.g., from about 200 milligrams to about 2,000 milligrams, from about 200 milligrams to about 1800 milligrams, from about 200 milligrams to about 1600 milligrams, from about 200 milligrams to about 1400 milligrams, from about 200 milligrams to about 1200 milligrams, from about 200 milligrams to about 1100 milligrams, from about 200 milligrams to about 1000 milligrams, from about 200 milligrams to about 900 milligrams, from about 100 milligrams to about 800 milligrams, from about 200 milligrams to about 700 milligrams, from about 200 milligrams to about 600 milligrams, from about 200 milligrams to about 500 milligrams, from about 200 milligrams to about 400 milligrams, from about 200 milligrams to about 300 milligrams) of panthenol.

In some embodiments, the methods can include administration of from about 400 milligrams to about 2,000 milligrams (e.g., from about 400 milligrams to about 2,000 milligrams, from about 400 milligrams to about 1800 milligrams, from about 400 milligrams to about 1600 milligrams, from about 400 milligrams to about 1400 milligrams, from about 400 milligrams to about 1200 milligrams, from about 400 milligrams to about 1100 milligrams, from about 400 milligrams to about 1000 milligrams, from about 400 milligrams to about 900 milligrams, from about 400 milligrams to about 800 milligrams, from about 400 milligrams to about 700 milligrams, from about 400 milligrams to about 600 milligrams) of panthenol.

In some embodiments, the methods can include administration of from about 500 milligrams to about 2,000 milligrams (e.g., from about 500 milligrams to about 2,000 milligrams, from about 500 milligrams to about 1800 milligrams, from about 500 milligrams to about 1600 milligrams, from about 500 milligrams to about 1400 milligrams, from about 500 milligrams to about 1200 milligrams, from about 500 milligrams to about 1100 milligrams, from about 500 milligrams to about 1000 milligrams, from about 500 milligrams to about 900 milligrams, from about 500 milligrams to about 800 milligrams, from about 500 milligrams to about 700 milligrams, from about 500 milligrams to about 600 milligrams) of panthenol.

In some embodiments, the methods can include administration of from about 600 milligrams to about 2,000 milligrams (e.g., from about 600 milligrams to about 2,000 milligrams, from about 600 milligrams to about 1800 milligrams, from about 600 milligrams to about 1600 milligrams, from about 600 milligrams to about 1400 milligrams, from about 600 milligrams to about 1200 milligrams, from about 600 milligrams to about 1100 milligrams, from about 600 milligrams to about 1000 milligrams, from about 600 milligrams to about 900) of panthenol.

In some embodiments, the methods can include administration of from about 700 milligrams to about 2,000 milligrams (e.g., from about 700 milligrams to about 2,000 milligrams, from about 700 milligrams to about 1800 milligrams, from about 700 milligrams to about 1600 milligrams, from about 700 milligrams to about 1400 milligrams, from about 700 milligrams to about 1200 milligrams, from about 700 milligrams to about 1100 milligrams, from about 700 milligrams to about 1000 milligrams, from about 700 milligrams to about 900) of panthenol.

In some embodiments, the methods can include administration of from about 800 milligrams to about 2,000 milligrams (e.g., from about 800 milligrams to about 2,000 milligrams, from about 800 milligrams to about 1800 milligrams, from about 800 milligrams to about 1600 milligrams, from about 800 milligrams to about 1400 milligrams, from about 800 milligrams to about 1200 milligrams, from about 600 milligrams to about 1100 milligrams, from about 800 milligrams to about 1000 milligrams) of panthenol.

In some embodiments, the methods can include administration of from about 900 milligrams to about 2000 milligrams (e.g., from about 900 milligrams to about 2,000 milligrams, from about 900 milligrams to about 1800 milligrams, from about 900 milligrams to about 1600 milligrams, from about 900 milligrams to about 1400 milligrams, from about 900 milligrams to about 1200 milligrams, from about 900 milligrams to about 1100 milligrams, from about 900 milligrams to about 1000 milligrams) of panthenol.

In some embodiments, the methods can include administration of from about 1000 milligrams to about 2000 milligrams (e.g., from about 1000 milligrams to about 2000 milligrams, from about 1000 milligrams to about 1800 milligrams, from about 1000 milligrams to about 1600 milligrams, from about 1000 milligrams to about 1400 milligrams, from about 1000 milligrams to about 1200 milligrams, from about 1000 milligrams to about 1100 milligrams) of panthenol.

In some embodiments, the methods can include administration of at least about 100 milligrams (e.g., at least about 200 milligrams, at least about 250 milligrams, at least about 300 milligrams, at least about 400 milligrams, at least about 500 milligrams, at least about 600 milligrams, at least about 700 milligrams, at least about 800 milligrams, at least about 900 milligrams, at least about 1000 milligrams). In certain embodiments, the methods can include administration of at least about 400 milligrams of panthenol (e.g., at least about 500 milligrams, at least about 800 milligrams, at least about 1000 milligrams) of panthenol.

In some embodiments, the methods can include administration of at least about 400 milligrams (e.g., at least about 500 milligrams, at least about 600 milligrams, at least about 700 milligrams, at least about 800 milligrams, at least about 900 milligrams, at least about 1000 milligrams). In certain embodiments, the methods can include administration of at least about 400 milligrams of panthenol (e.g., at least about 500 milligrams, at least about 800 milligrams, at least about 1000 milligrams) of panthenol.

In certain embodiments, the methods can include administration of from about 100 milligrams to about 1200 milligrams of panthenol.

In certain embodiments, the methods can include administration of from about 100 milligrams to about 400 milligrams (e.g., from about 200 milligrams to about 300 milligrams, e.g. about 250 milligrams) of panthenol.

In certain embodiments, the methods can include administration of from about 400 milligrams to about 1200 milligrams of panthenol.

In certain embodiments, the methods can include administration of from about 400 milligrams to about 600 milligrams (e.g., from about 450 milligrams to about 550 milligrams, e.g. about 500 milligrams) of panthenol.

In certain embodiments, the methods can include administration of from about 700 milligrams to about 1200 milligrams of panthenol.

In certain embodiments, the methods can include administration of from about 700 milligrams to about 900 milligrams (e.g., from about 750 milligrams to about 850 milligrams, e.g. about 800 milligrams) of panthenol.

In certain embodiments, the methods can include administration of from about 900 milligrams to about 1100 milligrams (e.g., from about 950 milligrams to about 1050 milligrams, e.g. about 1000 milligrams) of panthenol.

Injectable Compositions

In general, the compositions used in the methods described herein are in a form suitable for injection, e.g., in the form of a sterile injectable preparation, for example, as a sterile injectable aqueous solution or a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a nontoxic parenterally acceptable diluent or solvent, for example, as a solution in water or 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In some embodiments, an injectable composition can prepared by dissolving the active ingredient, i.e., panthenol in a suitable solvent (e.g., water).

Site of Administration

In some embodiments, an injectable composition containing the active ingredient (panthenol or a prodrug thereof) can be injected directly into the affected joint by intraarticular injection. For example, the injectable composition can be injected directly into the joint capsule (sometimes referred to as a "capsule of the joint" or "articular capsule") of the affected joint by intra-articular injection. As used herein, the terms "joint capsule," "capsule of the joint," or "articular capsule" each refer to the two-layer structure that completely envelopes the freely movable bone joints. The outer layer of the joint capsule is typically referred to as the stratum fibrosum and is composed of white fibrous tissue. The inner layer of the joint capsule is typically referred to as stratum synoviale, which is a secreting layer.

In other embodiments, the injectable composition containing the active ingredient (panthenol or a prodrug thereof) is not directly injected into the affected joint by intraarticular injection. Rather, the injection is made at a site that is outside of the affected joint, but still within the region of (e.g., in the vicinity of, next to, adjacent to, or closely adjacent to) the affected joint.

In some embodiments, the body region that serves as the site of the injection can be any body region surrounding the joint that is within about 20 millimeters (e.g. within about 19, about 18, about 17, about 16, about 15, about 14, about 13, about 12, about 11, about 10, about 9, about 8, about 7, about 6, about 5, about 4, about 3, about 2, or about 1 millimeters, e.g., about 10 millimeters) in any direction from the affected joint or from the exterior surface of any associated housing structure enveloping the affected joint, such as a joint capsule.

In certain embodiments, the site of the injection can be any body region surrounding the joint that is within at most about 15 millimeters (e.g. within at most about 10, 9, 8, 7, 6, 5, 4, 3, 2 or 1 millimeters, e.g., within at most about 10 millimeters or within at most about 5 millimeters) from the affected joint or from the exterior surface of any associated housing structure enveloping the affected joint, such as a joint capsule. For example, the site can be located outside of the joint capsule of the affected joint and within, e.g., about 5, 10, or 15 millimeters, e.g., about 5 millimeters, from the exterior surface of the stratum fibrosum of the joint capsule. While not wishing to be bound by theory, it is believed that the active ingredient can penetrate the joint by diffusion in this mode of administration.

In some embodiments, the site of injection can be determined on the basis of the size of the affected joint. For large joints, which can include the majority joints except for vertebrae, the injectable pharmaceutical composition may be injected into the capsule of the joint by intra-articular injection. For small joints, typically the vertebrae, injection outside of the joint or joint capsule is preferred, typically to avoid the risk of damage to the joint. This mode of administration also enables the use of large doses (and hence large volume injections), which would be otherwise difficult to accommodate in small joints. Typically the injection site for either mode of administration can be selected by the practitioner applying finger pressure to the joint, and asking the patient to identify the location of maximum pain.

Regimen

Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon, e.g., the host treated. A typical preparation will contain from about 5% to about 95% active ingredient (w/w). Alternatively, such preparations contain from about 20% to about 80% active ingredient.

In some embodiments, a typical dose is an aqueous solution (about 2 milliliters) containing about 500 mg of panthenol (e.g., dexpanthenol) or an aqueous solution (about 4 milliliters) containing about 1000 mg of panthenol (e.g., dexpanthenol). Lower doses can also be used (e.g., 250 mg of panthenol). The aqueous solution can be injected directly into the site of the inflamed joint or outside of the joint as described herein. A program of injections is generally desirable in which dosages similar to that indicated above are given at intervals of a few days (e.g., 2, 3, 4, 5, or 6 days) to about one week. Reduced inflammation and increased freedom of movement is typically noticeable within 48 hours from the initial injection. Using the 1000 mg dose, patients have reported an estimated 80% reduction of pain after the first injection. In certain embodiments, for larger doses (e.g., ≥1000 milligrams), the active ingredient can be provided in two or more closely spaced (e.g., from about 5 minutes to about 1 hour) and smaller doses (e.g., each independently about 400, about 500, or about 600 milligrams).

In some embodiments, the active ingredient (e.g., panthenol or a prodrug thereof) can be coadministered with one or more other therapeutic agents (e.g., local anesthetic, cysteine, glucosamine, a surface active phospolipid).

In certain embodiments, the additional agents may be administered separately, as part of a multiple dose regimen, from the panthenol (e.g., sequentially, e.g., on different overlapping schedules with the administration of the panthenol active ingredients described herein). Alternatively, these agents may be part of a single dosage form, mixed together with the panthenol active ingredients described herein in a single composition. In still another embodiment, these agents can be given as a separate dose (a separate injection) that is administered at about the same time that the panthenol active ingredients described herein are administered (e.g., simultaneously with the administration of the panthenol active ingredients described herein).

When the compositions of this invention comprise a combination of the panthenol active ingredients described herein and one or more additional therapeutic or prophylactic agents, both the panthenol active ingredients described herein and the additional agent can be present at dosage levels of between about 1 to 100%, and more preferably between about 5 to 95% of the dosage normally administered in a monotherapy regimen.

In certain embodiments, the initial treatment may cause some pain and it may, therefore, be desirable to co-administer a local anesthetic, e.g. bupivacaine or lignocaine, at the same time or shortly before the injection of the panthenol or prodrug thereof (e.g., as a separate injection), or as a co-formulation with the panthenol. For example, to provide short-term pain relief during the course of the injection, and/or so as to negate any pain due to the piercing effect of the injection itself, a suitable injectable formulation comprises 4 mls of 1000 mg of dexpanthenol and 1 mg of bupivacaine, for example, as an aqueous solution containing 250 mg/ml. dexpanthenol and 1 ml of a solution containing 5 mg of bupivacaine. In certain embodiments, 1 ml of 0.1% bupivacaine (providing 1 mg of bupivacaine) or 2 ml of 0.5% bupivacaine (providing 10 mg of bupivacaine) can be used in conjunction with 4 mL of an aqueous solution containing 250 mg/ml of dexpanthenol (providing 1000 mg of dexpanthenol).

Alternatively the bupivacaine, or other local anesthetic can be administered as a separate injection immediately before an injection of dexpanthenol.

In certain embodiments, other physiologically active materials may be co-administered, e.g. cysteine or glucosamine.

In certain embodiments, when injecting into a joint, it may also be helpful to co-administer within the same treatment regime, a surface active phospholipid (SAPL) such as dipalmitoyl-phosphatidyl choline (DPPC) or phosphatidyl glycerol (PG). Preferably, a mixture of DPPC and PG is employed. A preferred protein-free SAPL composition comprising a blend of DPPC and PG is available from Britannia Pharmaceuticals Ltd of Brighton Road, Redhill under the trade name 'pumactant'. While not wishing to be bound by theory, SAPL's such as 'pumactant' are believed to act as a lubricant in joints, taking over to some extent the function of synovial fluid.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The invention is further illustrated by the following Examples. The Examples are provided for illustrative purposes only, and are not to be construed as limiting the scope or content of the invention in any way.

Example 1

62 patients (26 men; 33 women) aged 21 to 85 years were treated for traumatic inflammatory conditions. The patients were administered one or more intra-articular or peri-articular injections, i.e., into the inflamed joint or nearby area, of dexpanthenol in combination with a long acting local anesthetic [4 ml of an aqueous solution of dexpanthenol Ph Eur (equal to 1 g of dexpanthenol); 1 ml of 0.1% bupivacaine].

In terms of pain relief following injection, efficacy outcome of the treatment is shown in the table below:

| | | | Outcome | | | |
|---|---|---|---|---|---|---|
| Site of complaint | n* | Improved n (%) | Temporarily improved n (%) | No change n (%) | Worsened n (%) | Not reported n (%) |
| Back (post-traumatic spondylitis) | 54 | 30 (55.6) | 6 (11.1) | 6 (11.1) | 3 (5.6) | 9 (16.7) |

-continued

|  | | Outcome | | | | |
| Site of complaint | n* | Improved n (%) | Temporarily improved n (%) | No change n (%) | Worsened n (%) | Not reported n (%) |
| --- | --- | --- | --- | --- | --- | --- |
| Hip | 22 | 9 (40.9) | 4 (18.2) | 2 (9.1) | 2 (9.1) | 5 (22.7) |
| Knee | 8 | 5 (62.5) | 0 (0) | 1 (12.5) | 0 (0) | 2 (25.0) |
| Other | 14 | 5 (35.7) | 3 (21.4) | 1 (7.1) | 1 (7.1) | 4 (28.6) |
| Total | 98 | 49 (50.0) | 13 (13.2) | 10 (10.2) | 6 (6.1) | 20 (20.4) |

*Some patients reported more than one site

In this cohort of patients, 87% of patients complained of back pain, which was often accompanied by pain in other joints or sites. Where reported, about three-quarters of all patients benefited from pain relief, while less than 10% said that their condition had worsened. Several patients mentioned that they experienced improvement after the initial injection, which continued to improve with time. Although, in most cases, the complaint was reported as 'improved' only, there was indication that several patients had considerable benefit from the treatment.

From case notes of the 62 patients, injections into the joint or nearby area of dexpanthenol in combination with bupivacaine was generally safe and well tolerated. Five (8%) of the 62 patients reported adverse events, including numbness and injection site pain, which resolved with time.

Injection of facet joints has previously almost invariably been done using MRI to ensure exact placing of the needle. However in the above testing it was found that facet joints are easily treated by injection without the use of MRI. By palpating the patient's back in the area of pain and spasm, there is often an area of extreme tenderness about 5 cms from the midline, indicating the site of the inflamed facet joints. If a needle is inserted at right angles into this area, it will be located in or exceedingly close to the facet joint. The dexpantothenol solution does not have to be injected directly into the joint, as it will diffuse into the joint from an injection adjacent to it; both are equally effective.

Example 2

The cohort of patients assessed in Example 1 primarily reported back pain to the test physician. Treatment of some patients who reported specific joint pain is summarised below. Bepanthene is a aqueous solution containing 250 mg/ml of dexpanthenol Ph Eur; 4 mls bepanthene provides 1000 mg dexpanthenol. An injection of 2 mls of 0.5% bupivacaine provides 10 mg bupivacaine.

Hip Pain
Injection—4 ml bepanthene, 2 ml of 0.5% bupivacaine.
Patient 1—hip—1 injection—"considerable relief" straight away.
Patient 2—left hip—1 injection—"immediate improvement."
Patient 3—right hip—1 injection—"hip improving, no sudden change after injection."
Patient 4—right hip—1 injection—"hip better."
Tennis Elbow
Injection—1-2 ml bepanthene, 0.5-1 ml of 0.5% bupivacaine. When administering an injection of 2 mls containing 500 mg dexpanthenol, if the injection is painful, it may be appropriate to discontinue the injection at delivery of 1 ml, providing 250 mg of dexpanthenol, and repeat the dose at a later time.

Patient 1—both elbows injected—better.
Patient 2—4 injections—full recovery.
Patient 3—right elbow—2 injections—better.
Patient 4—right elbow—2 injections—better.
Shoulder Pain
Injection into Capsule—4 ml bepanthene, 2 ml of 0.5% bupivacaine.
Injection adjacent Capsule (into Tendon)—1-2 ml bepanthene, 0.5-1 ml of 0.5% bupivacaine.
Patient 1—left shoulder—2 injections—improved.
Patient 2—12 injections over 6 months—95% improvement.
Ankle Pain
Injection—4 ml bepanthene, 2 ml of 0.5% bupivacaine.
Patient 1—1 injection—better.
Patient 2—2 injections—better.
Patient 3—1 injection—better.
Patient 4—9 injections over 2-months 90% improvement.
Knee Pain
Injection—4 ml bepanthene, 2 ml of 0.5% bupivacaine.
Patient 1—right knee 3 injections, left knee 2 injections—"knees have been feeling a lot better."

Other Embodiments

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating pain in a joint inflamed by traumatic arthritis which comprises injecting a solution comprising at least about 500 mg of panthenol into the inflamed joint, or injecting the solution into a site that is next to the inflamed joint but outside the capsule of the inflamed joint.

2. The method of claim 1, wherein the solution is injected directly into the inflamed joint.

3. The method of claim 1, wherein the solution is injected into a site that is next to the inflamed joint but outside the capsule of the inflamed joint.

4. The method of claim 3, wherein the solution is injected into a site that is within about 10 millimeters from the exterior surface of the capsule of the inflamed joint.

5. The method of claim 1, wherein the solution is an aqueous solution.

6. The method of claim 1, wherein the panthenol is co-formulated with a local anaesthetic.

7. The method of claim 1, wherein a local anaesthetic is co-administered with the panthenol in a separate injection.

8. The method of claim 1, wherein the solution comprises about 1000 mg of panthenol.

9. The method of claim 1, wherein the inflamed joint is a freely moving joint that is inflamed by traumatic arthritis.

10. The method of claim 1, wherein the panthenol is dextro-panthenol (dexpanthenol).

11. The method of claim 1, wherein a formulation comprising 1000 mg of dexpanthenol and 5 mg of bupivacaine is injected.

\* \* \* \* \*